(12) United States Patent
Sweitzer (10) Patent No.: US 10,987,231 B2
(45) Date of Patent: Apr. 27, 2021

(54) LOCKING GRIP ORTHOPEDIC IMPLANT EXTRACTION TOOL

(71) Applicant: Shukla Medical, St. Petersburg, FL (US)

(72) Inventor: Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 64 days.

(21) Appl. No.: 16/110,311

(22) Filed: Aug. 23, 2018

(65) Prior Publication Data

US 2018/0360620 A1 Dec. 20, 2018

Related U.S. Application Data

(63) Continuation of application No. 15/058,830, filed on Mar. 2, 2016, now Pat. No. 10,085,852.

(60) Provisional application No. 62/135,793, filed on Mar. 20, 2015.

(51) Int. Cl.
*A61F 2/46* (2006.01)
*A61F 2/30* (2006.01)

(52) U.S. Cl.
CPC .... *A61F 2/461* (2013.01); *A61F 2002/30476* (2013.01); *A61F 2002/30537* (2013.01); *A61F 2002/4619* (2013.01); *A61F 2002/4622* (2013.01); *A61F 2002/4681* (2013.01)

(58) Field of Classification Search
CPC ... A61B 17/8875; A61B 17/1606; A61F 2/46; A61F 2002/4622
See application file for complete search history.

(56) References Cited

U.S. PATENT DOCUMENTS

| | | | | |
|---|---|---|---|---|
| 4,263,705 A | * | 4/1981 | Devening | B25B 7/123 29/256 |
| 7,879,042 B2 | * | 2/2011 | Long | A61F 2/4607 606/99 |
| 7,942,083 B2 | * | 5/2011 | Jordan | B25B 7/02 29/227 |

* cited by examiner

*Primary Examiner* — Andrew Yang
(74) *Attorney, Agent, or Firm* — Kim IP Law Group LLC (57) ABSTRACT

A locking grip extraction tool has plier handles with jaws having sharp beveled edges for moving in a direction so that an axis perpendicular to the plane of movement is oriented at an acute angle to the handles; the axis intersecting the plane of jaw movement at a point midway between the jaws. A locking link coupled to the handles is adapted to releasably lock the jaws onto an orthopedic implant. A connection rod can be threaded into a hole in one of the handles near the jaws, so that a force applying tool such as a slap hammer can be connected to the rod to apply force to remove the implant. The rod is in alignment with the axis, which alignment makes it easier to remove the implant.

15 Claims, 9 Drawing Sheets

LOCKING GRIP ORTHOPEDIC IMPLANT EXTRACTION TOOL

CROSS-REFERENCE TO RELATED APPLICATIONS

This application is a continuation of U.S. patent application Ser. No. 15/058,830, filed Mar. 2, 2016 and entitled "Locking Grip Orthopedic Implant Extraction Tool," which claims priority under 35 U.S.C. § 119(e) to U.S. Provisional Application Ser. No. 62/135,793, filed Mar. 20, 2015 and entitled "Locking Grip Orthopedic Implant Extraction Tool," the disclosures of each of which are hereby incorporated by reference in their entirety.

BACKGROUND OF THE INVENTION

The present invention relates to a tool for facilitating the removal of an orthopedic implant used in joint surgery.

When a joint implant needs to be replaced, the surgeon needs to remove it, and removal can be difficult because the implant is fixed to adjacent bone by bone cement and/or bone in-growth.

Current devices which allow the implant to be gripped so that force can be applied to remove it, don't adequately grasp or hold the implant, and tend to slip off or not optimally allow for application of removal force. While vise-grip pliers have been used to remove orthopedic pins, they are generally not suitable for removal of other types of implants.

Accordingly, an object of the present invention is to provide a tool for temporarily and securely connecting a joint implant to a force applying tool such as a slide hammer that can provide sufficient impact to drive the implant out.

BRIEF SUMMARY OF THE DISCLOSURE

As herein described, a tool is provided for removing an orthopedic implant secured to a bone which forms part of a joint. The tool has handles with ends having opposing jaws which move in a direction at an acute angle to the handles. A lever locking mechanism releasably can lock the handles in place after the jaw edges engage an implant; at which time an extraction device can be connected to one of the handles near the jaws, to drive the implant out.

BRIEF DESCRIPTION OF THE DRAWINGS

FIGS. 1 to 4 show a first embodiment of the invention, wherein:

FIGS. 5 to 8D show a second embodiment of the invention having modular jaws, wherein:

FIGS. 9 to 13 show the tool of FIGS. 1 to 4 with the addition of a slide action locking mechanism to temporarily and securely hold the tool handles in a locked position, wherein:

DETAILED DESCRIPTION OF THE DISCLOSURE

First Embodiment—FIGS. 1 Through 4

As shown FIGS. 1 to 4 the locking grip pliers tool 20 has an upper handle 21 and a more massive lower or gripping handle 22 joined to the upper handle by a locking link 23 which cooperates with the handles to provide a locking grip mechanism. A first jaw 24A is affixed to an implant gripping end of the handle 21, while a second jaw 24B is pivotably mounted to the adjacent end of the gripping handle 22 for rotation about the pins 34 and 26.

The knee joint 27 includes the proximal ends of the tibia 28 and fibula 29, and the distal end of the femur 30. A metal orthopedic implant 31 has a base or tray 31A and a stem 31B which is embedded in the truncated proximal end of the tibia 28. The jaws 24A and 24B engage, and have sharp edges which extend below opposite sides of the implant tray 31A.

The locking link 23 has one end mounted for rotation about the pin 51 in the gripping handle 22, while the other end is T-shaped and slidably installed in a longitudinal groove in the upper handle 21. A mechanical stop 32 secured within the gripping handle prevents the jaws from closing any further past the adjusted opening controlled by thumb screw 33.

The thumb screw 33 in the end of the upper handle remote from the jaws extends into the longitudinal slot to adjustably limit the range of movement of the locking link 23, which serves to limit the extent to which the jaws may be closed.

When the handles are moved toward each other to cause the jaws 24A, 24B to grip the implant tray 31A, a compressive force will be applied to link 23. This compressive force will be a maximum when link 23 is parallel to the imaginary line drawn between pin 26 and pin 34 that connects to the gripping handle 22. As the handles are pulled further (closer together) past this point, the compressive force is reduced and travel of the handles is arrested when stop 32 contacts link 23. At this position the tool is locked and the compressive force on link 23 is what prevents the handles from re-opening. The handles may be released from their locked position by applying sufficient force to pull them apart or by pulling member 35 (which is affixed to the end of handle 22 remote from the jaws) toward handle 21, which unlocks the jaws.

The upper handle 21 has a threaded hole 36 in the end adjacent the jaws, the axis X-X of which hole is aligned at an acute angle α to the handle. A connection rod 37 may have a lower threaded end that engages with the threads of the hole 36, so that when the implant tray 31A has been grasped by the jaws 24A and 24B, the connection rod is axially aligned with the implant stem 31B.

The locking grip mechanism works in a manner similar to that of vise grip locking pliers. The jaws of the tool are similar to those of regular pliers and adjust to the rough outer dimension of the implant and lock down onto it, to hold it firmly so that the surgeon can let go of the tool and it will stay in place, gripping the implant tray. The jaws are designed to grip orthopedic implants, the embodiments described herein being for use in knee surgery.

The jaws 24A, 24B are shaped with sharp edges so they can penetrate into the interface 38 under the implant tray 31A. This interface may consist of an implant-bone cement boundary or an implant-bone boundary. The force generated by the handles provides a mechanical advantage to perform this function. The jaws have a width allowing them to fit into spaces on the implant or to fit around a length of the implant in order to provide a strong grip on the implant. The sharp edges allow greater pressure to be transferred to the material adjacent the implant to facilitate implant removal, than if only the outside edges of the implant were gripped.

Figure 1:
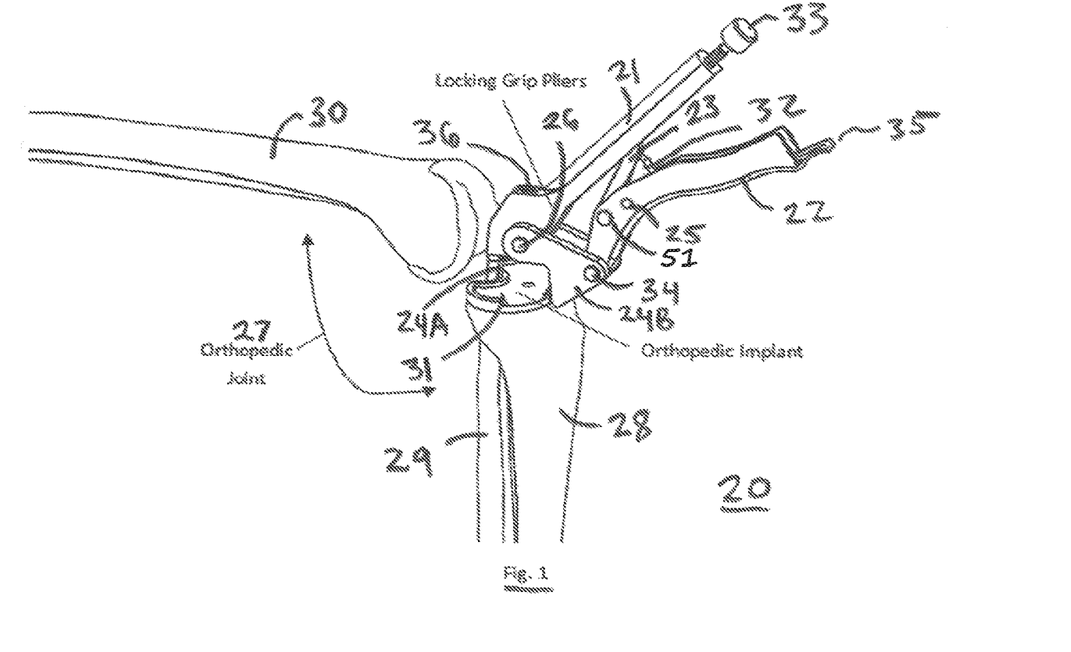
FIG. 1 is an isometric view of the tool in position for gripping an orthopedic implant to be removed from the knee joint of a patient.
Figure 2:
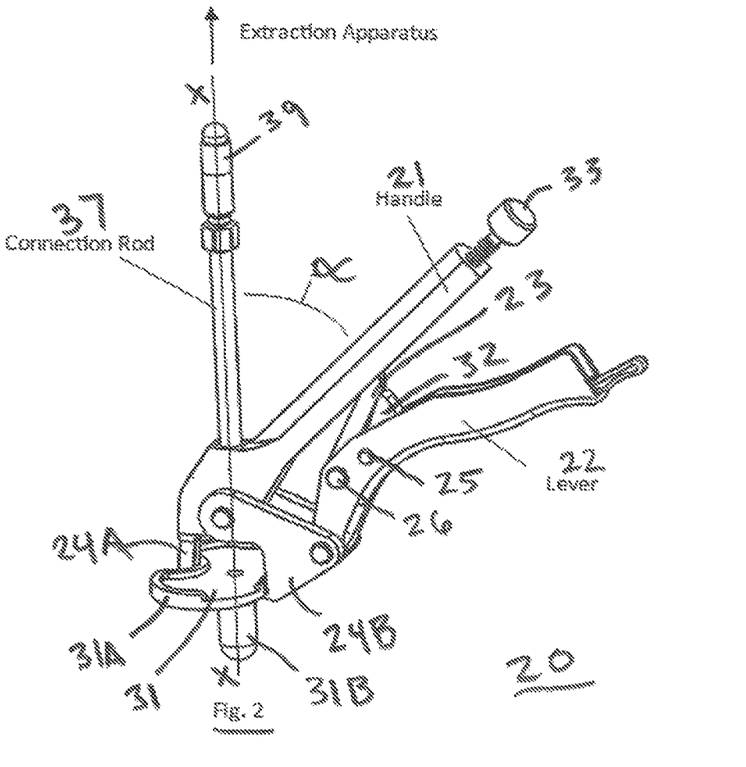
FIG. 2 is an isometric view of the tool gripping the implant, with a connection rod attached for coupling to a slide hammer for applying extraction force to the tool jaws, and thus to the implant.

Once the tool 20 is firmly secured to the implant, one end of the threaded rod 37 is threaded into the hole 36 to connect the rod to the part of the tool near the jaws; and the other threaded end of the connection rod 37 is connected by means of the threaded connection member 39 to an extraction frame or slide hammer, which provides adequate force to remove the implant 31. The connection rod, with which the stem is in axial alignment, directs the extraction force to the implant so that the implant is removed cleanly, thus minimizing bone loss from the patient.

The handles 21, 22 of the tool are oriented at an acute angle with respect to a line orthogonal to the plane of movement of the jaws (that is, a line coinciding with the axis X-X of the connection rod 37), to allow proper orientation to the incision and the surgeon's hand. Preferably, the angle between the handles and a line orthogonal to the plane of movement of the jaws should be in the range of 30° to 60°. This angle also allows the connection rod to be connected at a point close to the jaws, which provides increased rigidity as compared to a connection at the end of one of the tool handles or on the tool adjustment screw 33.

Multiple jaw sizes can be manufactured to accommodate a wide variety of implant sizes.

The locking link 23 coupling the tool handles to each other is loaded by a compression spring within the longitudinal groove inside handle 21, to keep it pressed against the end of the adjustment screw 33 that extends into the groove of the handle 21. Otherwise the link would slide down through the groove and operation of the tool would be cumbersome.

For some implant removal situations the jaws may be straight instead of being curved, so as to grip the implant only on its sides, using friction to grasp it, if curved jaws would risk damaging a critical object under the implant.

The locking link 23 may have a bend, which would allow for a greater range of movement of the jaws, so that the tool can be completely released from the implant if the surgeon needs to adjust the grip tighter, or for general purposes of releasing the implant from the jaws.

Figure 3:
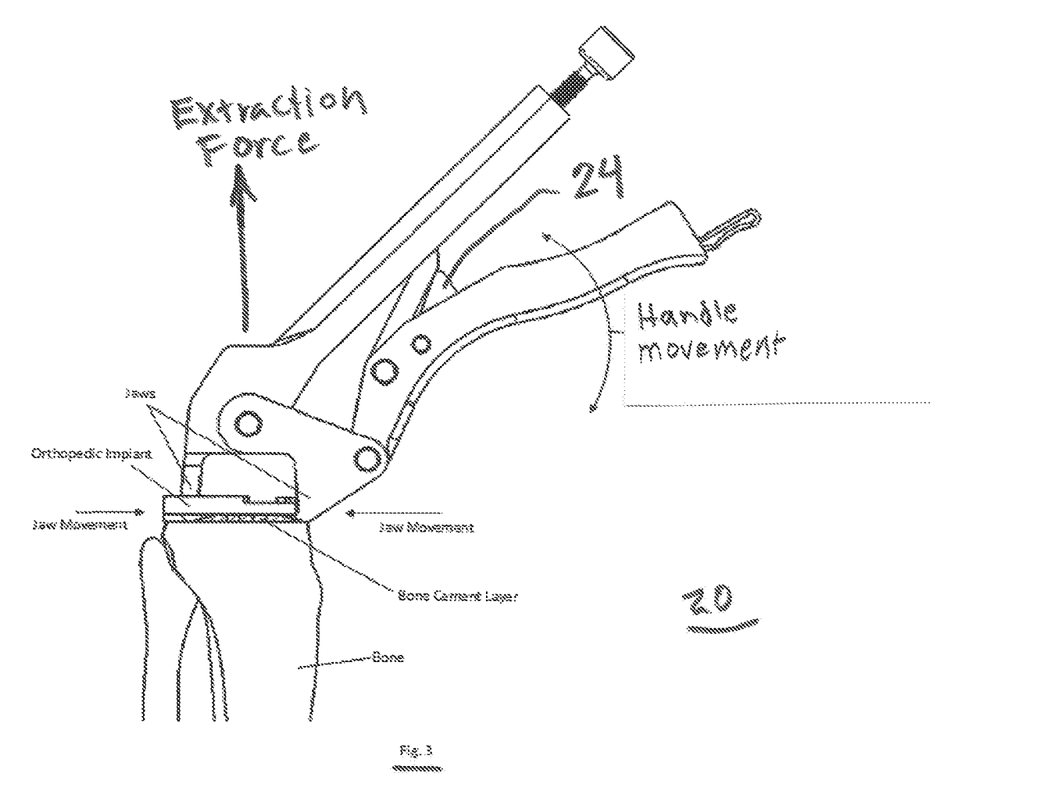
FIG. 3 is an isometric view similar to that of FIG. 1, showing the direction of movement of the jaws to penetrate bone cement below the implant.
Figure 4:
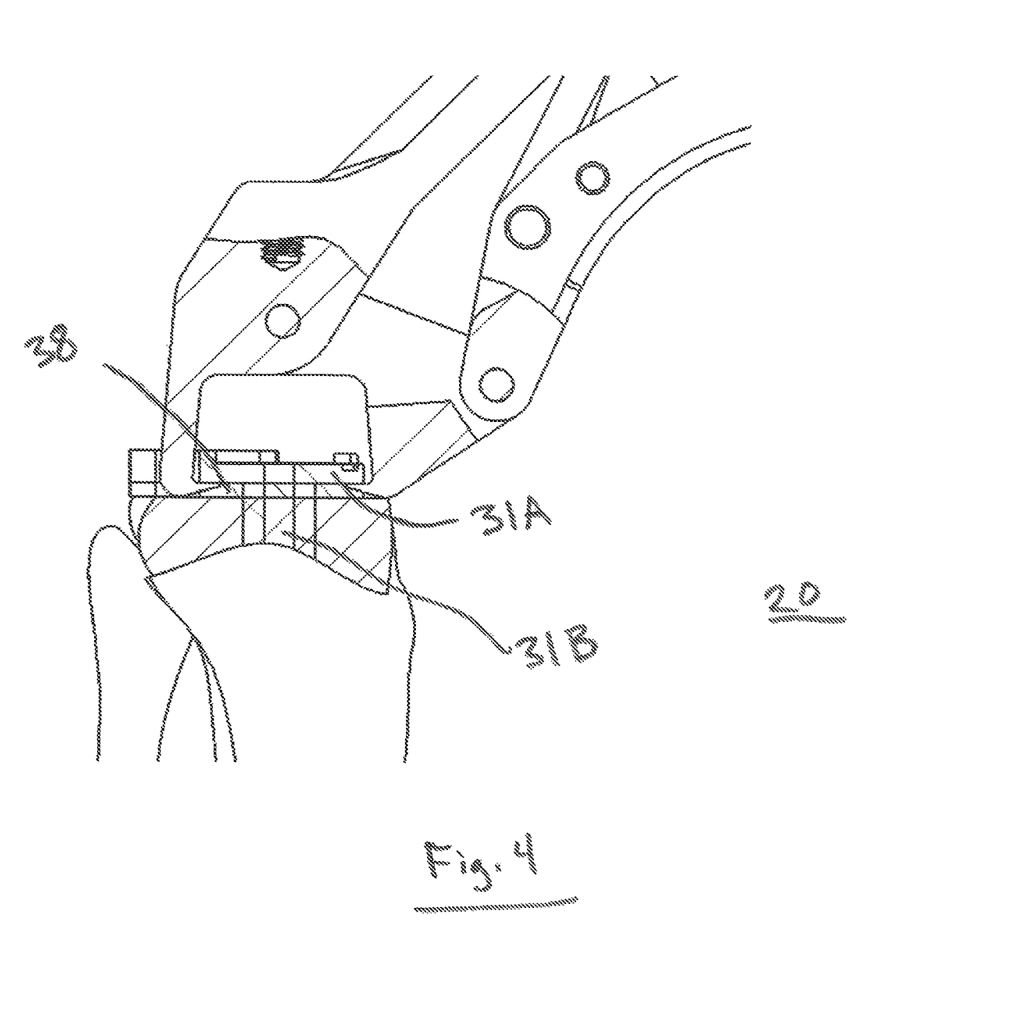
FIG. 4 is a breakaway isometric view that is similar to that of FIG. 3. The breakaway portion depth is half the width 3 of the tool, which allows a better visualization of the jaws which are shown extending under the implant.

As extraction force is applied to the connection rod by the slap hammer or other extraction device, it forces the jaws to close harder onto the implant, as shown in FIG. 3. This effect tightens the jaws onto the implant during extraction, reducing the risk of the jaws slipping off the implant.

Angling the handles with respect to the jaws 24A, 24B and connection rod receiving hole 36 (see angle α, depicting the angle of the handle relative to the connection rod) allows the implant to be extracted in the optimum direction when an extraction force is applied. This orientation of the connection rod—with its axis X-X perpendicular to the plane of movement of the jaws and intersecting that plane at a point midway between the jaws—also results in application of extraction force in a direction perpendicular to the force applied to the implant by the tool jaws so that interaction of the extraction force with the gripping handle and jaws facilitates removal of the implant.

The angular orientation of the handles with respect to the connection rod and jaws provides improved rigidity because it allows the connection rod to be connected at a point close to the jaws, thus greatly reducing play which would be present if the rod were to be connected to the end of a handle; an improvement over the prior art in which an extraction device is connected to the adjustment screw of pliers, which screw is remote from the pliers jaws. In the present invention, since the adjustment screw is not connected to a slide hammer or the like, that screw can be easily adjusted without having to accommodate rotation of the slide hammer.

The angled configuration of the handles with respect to the connection rod and jaws allows access to difficult surgical entry sites that may be hard to get to with pliers having handles perpendicular to the jaws as in prior implant gripping tools.

The adjustment screw 33 has double lead threads which allow faster adjustment of the opening range of the jaws. This shortens the setup time of the tool and reduces the time for completion of the surgery.

Second Embodiment—FIGS. 5 to 8D

In the second embodiment shown in FIGS. 5 through 8D, the tool 50 has the same construction as the tool 20 of FIGS. 1 to 4, except that the jaws are replaceable.

Figure 5:
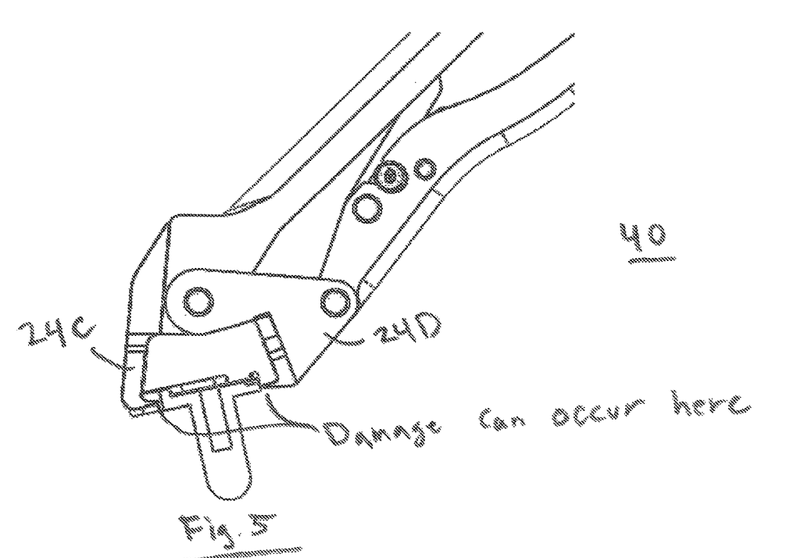
FIG. 5 is a partial isometric view showing the manner in which damage can occur to the jaw edges.

Over a period of time the jaws of the tool 20 can become damaged by the repetitive action of the jaws piercing under the implant, in and out of bone cement and/or bone, so that the jaws need to be replaced. Jaw damage can also occur if the surgeon mistakenly causes the jaws to be rammed into the sides of the implant tray as shown in FIG. 5. The mechanical advantage of the tool can result in so large a force being applied to the jaws that they are bent out of shape. In either of these scenarios, replacement of the jaws is more cost effective than replacement of the entire tool.

A change of jaws is sometimes needed when a different type of implant needs to be removed. Such an implant type may have "augments" in which the tray of the implant is relatively thick, requiring jaws with an extended reach. The ability to interchange different jaw types is a great advantage because it allows the operator to use the tool for different and sometimes difficult surgical cases.

The jaws can be made replaceable by creating an attachment interface wherein jaws of varying types can be readily interchanged. Some examples of interfaces can be "T-Slot," snap fit, magnetic, adhesively adhered, or using fasteners.

In the embodiment shown in FIGS. 5 through 8D, jaw interchange is effected by means of a mounting screw and an alignment or guide pin; namely the screw 41 and pin 42 for detachably securing the fixed jaw 24C and the screw 43 and pin 44 for detachably securing the movable jaw 24D.

Figure 6A:
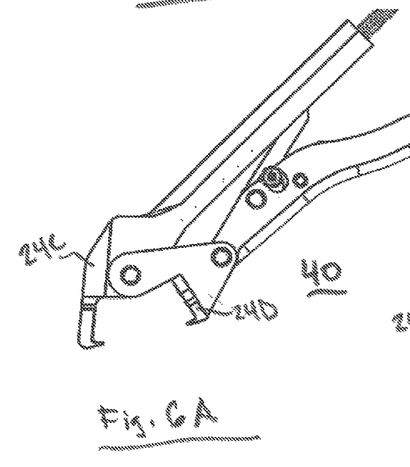
FIG. 6A is a partial isometric view showing the jaws in an open position.
Figure 6B:
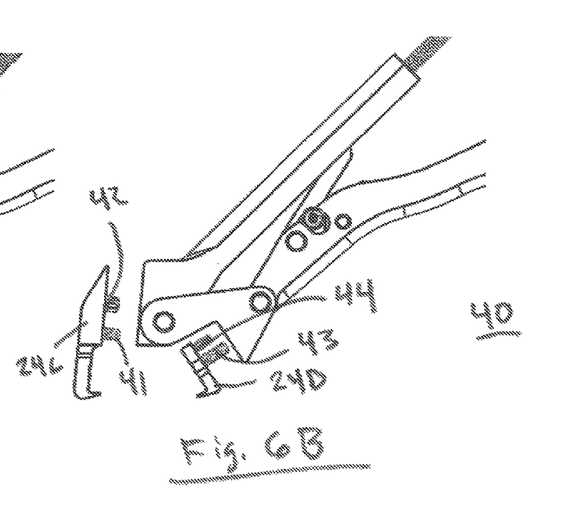
FIG. 6B is a partial isometric view showing the modular jaws ready for installation.
Figure 7:
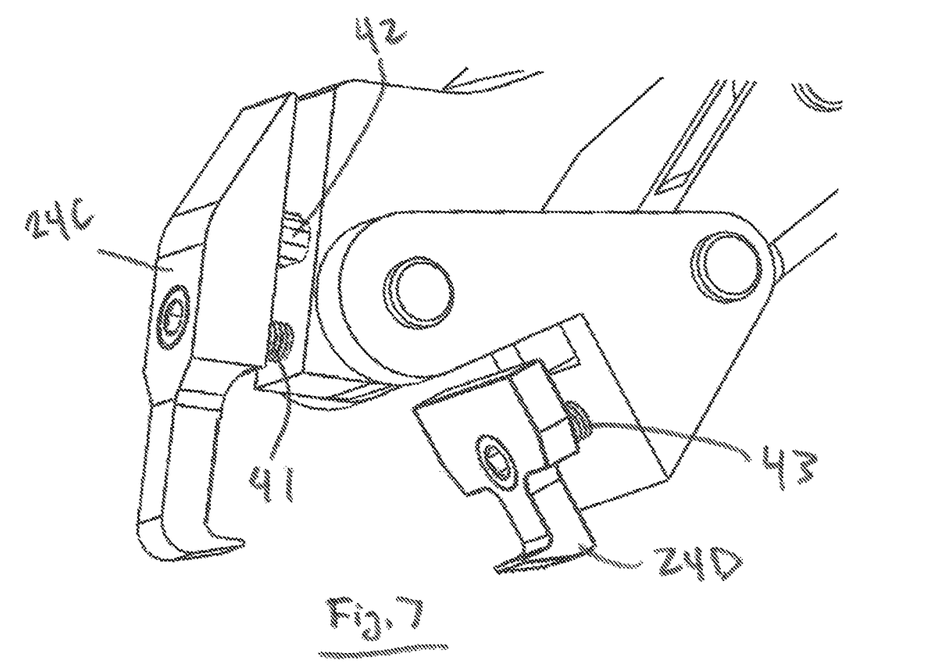
FIG. 7 is a partial isometric view showing the modular jaws in the process of being installed.
Figure 8A:
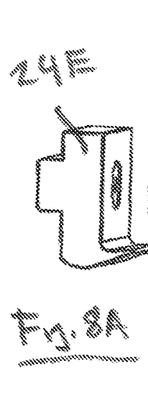
FIGS. 8A, 8B, 8C and 8D show various types and sizes of modular jaws.
Figures 8B, 8C, 8D:
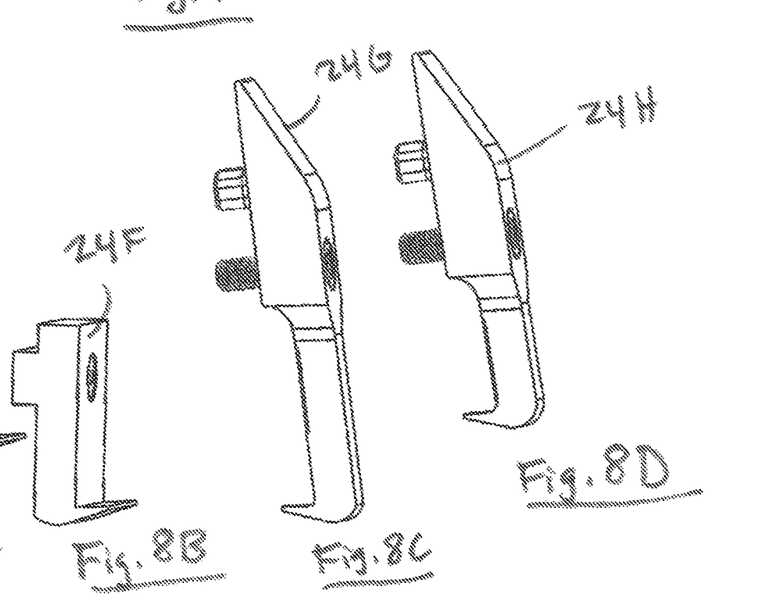
Figure 9:
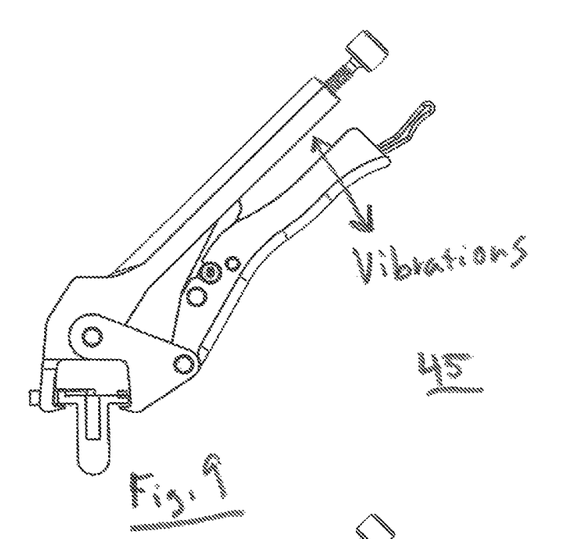
FIG. 9 is an isometric view of the tool in engagement with an implant, with the handles in closed position.

To change the jaws of the tool 40, the screws 41 and 43 are loosened and removed, and the jaws 24B and 24C are removed. Then replacement jaws are placed in position and secured with those screws, with the guide pins 42 and 44 engaging corresponding holes in the replacement jaws.

Third Embodiment—FIGS. 9 Through 13

Figure 10:
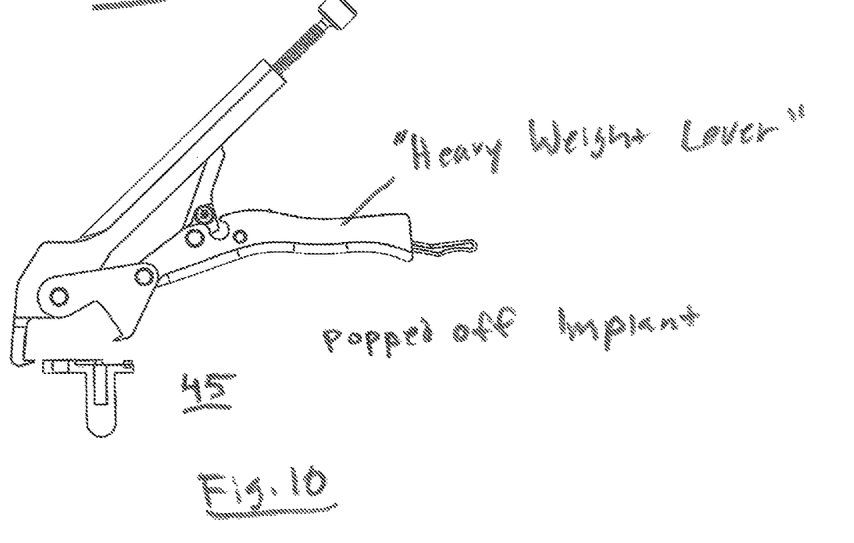
FIG. 10 is an isometric view which shows the tool of FIG. 9 with the handles in an open position after having popped open due to vibration while attempting to remove an implant.

During the operation of the tools 20 and 40 they are subjected to vibration due to repetitive impact force applied by the slap hammer or other extraction device, causing the gripping handle to pop loose.

To prevent such inadvertent release of the handles from their locked position, in the third embodiment the tool 45 adds a sliding rod 46 and a C-shaped detent 47. The rod 46 is mounted so that it can slide in a direction transverse to the handles 21 and 22 and act as a secure locking mechanism which, when engaged, prevents movement of the link relative to the gripping handle and thus securely locks the tool in its closed position.

Figure 13:
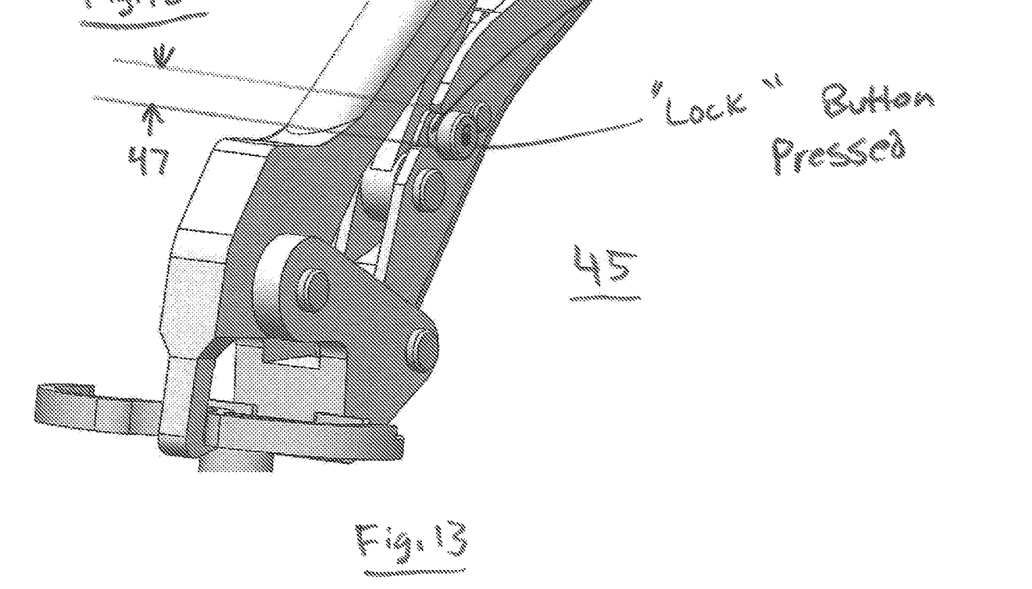
FIG. 13 is a partial isometric view showing the locking mechanism in the locked position.

When the secure locking mechanism is engaged by sliding the rod 46 so that its larger diameter portion 48 is retained in the undercut portion of the C-shaped detent 47, the locking link cannot move relative to the gripping handle and the handles therefore cannot move relative to each other; thus keeping the jaws firmly clamped onto the implant.

Figure 12:
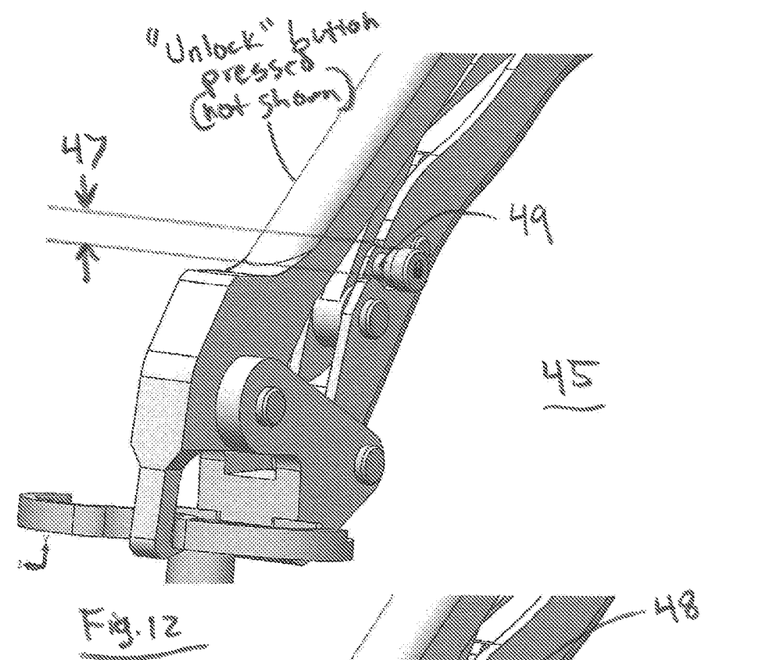
FIG. 12 is a partial isometric view showing the locking mechanism in the unlocked position.

The secure locking mechanism is disengaged by sliding the rod 46 so that its smaller diameter portion 49 is within the detent 47 and therefore free to pop out of that detent.

This secure locking mechanism functions the same way for every size implant engaged in the adjustable range of the tool.

Figures 11A, 11B, 11C:
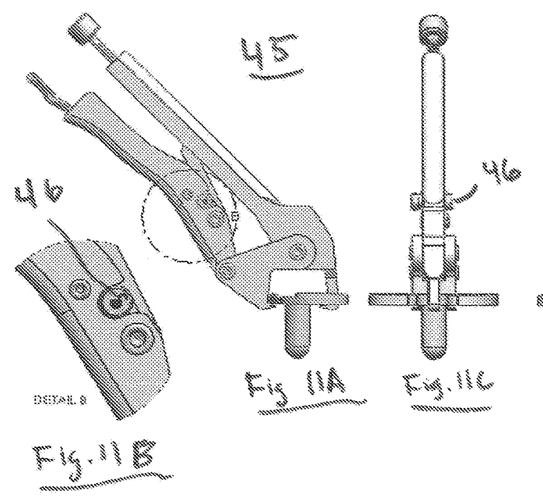
FIG. 11A is a left isometric view showing the end of the slidable locking mechanism which may be pushed to lock the handles in closed position.
FIG. 11B is an enlarged view of the part of the locking mechanism shown in FIG. 11A.
FIG. 11C is a front isometric view of the tool showing the slidable rod part of the locking mechanism.
Figures 11D, 11E:
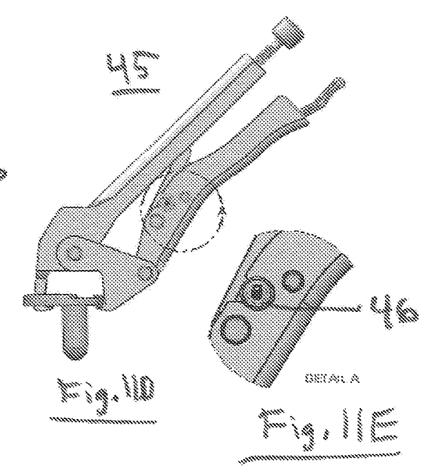
FIG. 11D is a right isometric view showing the end of the slidable locking mechanism which may be pushed to disengage the locking mechanism.
FIG. 11E is an enlarged view of the part of the locking mechanism shown in FIG. 11D.

Thus the secure locking mechanism functions similar to a safety switch on a firearm. The slidable rod 46 can be pushed like a button from either side of the gripping handle. The ends of this rod are labeled with lock symbols that show which way to push the rod to go between the locked and unlocked positions of the tool.

I claim:

1. An extraction tool for orthopedic implants comprising:
a first handle having a first jaw at a distal end of the first handle, wherein the first jaw has a first width defining a first implant engaging surface, and a first sharp edge extending substantially transverse to the first implant engaging surface;
a second handle pivotally coupled to the first handle about a fulcrum adjacent a distal end of the first and second handles, the second handle having a second jaw extending from a distal end of the second handle, wherein the second jaw has a second width defining a second implant engaging surface, and a second sharp edge extending substantially transverse to the second implant engaging surface;
a locking link coupling the first handle to second handle;
an adjustment screw operatively engaged with the locking link, wherein the adjustment screw includes double lead threads; and
a connection rod extending from and rigidly attached to the first handle, wherein a longitudinal axis of the connection rod extends substantially normal to a plane of movement defined by the first and second jaws.

2. The extraction tool of claim 1, wherein the second width of the second jaw is greater than the first width of the first jaw.

3. The extraction tool of claim 1, wherein the first and second sharp edges facingly engage each other.

4. The extraction tool of claim 1, wherein the longitudinal axis of the connection rod is substantially aligned with a plane defined by the first implant engaging surface.

5. The extraction tool of claim 1, wherein the second width of the second jaw is sized sufficiently to provide two spaced apart implant engaging surfaces.

6. The extraction tool of claim 5, wherein the first and second jaws provide three points of engagement for engaging an orthopedic implant.

7. The extraction tool of claim 1, wherein the first jaw includes a hook-like member.

8. The extraction tool of claim 1, wherein the second jaw includes a hook-like member.

9. The extraction tool of claim 1, wherein a longitudinal axis of the first handle extends about 30 to 60 degrees from the first implant engaging surface of the first jaw.

10. The extraction tool of claim 1, wherein the longitudinal axis of the connection rod is substantially aligned with the fulcrum.

11. The extraction tool of claim 1, wherein a longitudinal axis of the first handle is substantially aligned with the fulcrum.

12. The extraction tool of claim 1, wherein the longitudinal axis of the connection rod extends substantially about a midpoint between the first and second jaws.

13. The extraction tool of claim 1, wherein the longitudinal axis of the connection rod extends substantially parallel to the first and second implant engaging surfaces.

14. The extraction tool of claim 1, wherein a longitudinal axis of the first handle extends about 30 to 60 degrees from the longitudinal axis of the connection rod.

15. The extraction tool of claim 1, wherein a rotational axis of the fulcrum intersects the longitudinal axis of the connection rod.

* * * * *